(12) United States Patent
Lynes et al.

(10) Patent No.: US 7,655,421 B2
(45) Date of Patent: Feb. 2, 2010

(54) CYTOMETER ON A CHIP

(75) Inventors: Michael A. Lynes, Eastford, CT (US); Salvador M. Fernández, Hartford, CT (US)

(73) Assignee: Ciencia, Inc., East Hartford, CT (US)

( * ) Notice: Subject to any disclaimer, the term of this patent is extended or adjusted under 35 U.S.C. 154(b) by 188 days.

(21) Appl. No.: 11/454,329

(22) Filed: Jun. 16, 2006

(65) Prior Publication Data
US 2007/0026382 A1 Feb. 1, 2007

Related U.S. Application Data

(60) Provisional application No. 60/691,951, filed on Jun. 17, 2005.

(51) Int. Cl.
*G01N 33/53* (2006.01)
(52) U.S. Cl. .............................. 435/7.2; 435/2; 435/3; 435/7.1; 435/287.2; 435/374; 435/383; 435/395; 436/517; 436/524; 436/10; 436/15; 436/149; 436/164; 436/165; 436/171; 436/173; 422/82.11; 356/128; 356/130; 356/132; 356/136
(58) Field of Classification Search .................... 435/2, 435/3, 5, 6, 7.1, 7.2, 173.4, 285.2, 287.2; 436/517, 524, 63, 149, 164, 165, 171, 173; 422/55, 82.11; 359/245; 356/128, 130, 132, 356/136
See application file for complete search history.

(56) References Cited

U.S. PATENT DOCUMENTS

| | | | | |
|---|---|---|---|---|
| 4,931,384 A | * | 6/1990 | Layton et al. ............... 435/7.31 |
| 6,600,563 B1 | | 7/2003 | Bahatt et al. ................. 356/445 |
| 6,873,417 B2 | | 3/2005 | Bahatt et at ................. 356/445 |
| 6,982,819 B2 | | 1/2006 | Sawin et al ................. 359/245 |
| 7,057,786 B2 | * | 6/2006 | Sawin et al. ................. 359/245 |
| 7,251,085 B2 | | 7/2007 | Bahatt et al. ................. 359/809 |
| 7,349,080 B2 | * | 3/2008 | Aklian ....................... 356/128 |

FOREIGN PATENT DOCUMENTS

| | | | |
|---|---|---|---|
| WO | WO 01/32844 | * | 5/2001 |
| WO | WO 03/072699 A2 | * | 4/2003 |

* cited by examiner

*Primary Examiner*—Gailene R Gabel
(74) *Attorney, Agent, or Firm*—Alix, Yale & Ristas, LLP

(57) ABSTRACT

An assay technique for label-free, highly parallel, qualitative and quantitative detection of specific cell populations in a sample and for assessing cell functional status, cell-cell interactions and cellular responses to drugs, environmental toxins, bacteria, viruses and other factors that may affect cell function. The technique includes a) creating a first array of binding regions in a predetermined spatial pattern on a sensor surface capable of specifically binding the cells to be assayed; b) creating a second set of binding regions in specific spatial patterns relative to the first set designed to efficiently capture potential secreted or released products from cells captured on the first set of binding regions; c) contacting the sensor surface with the sample, and d) simultaneously monitoring the optical properties of all the binding regions of the sensor surface to determine the presence and concentration of specific cell populations in the sample and their functional status by detecting released or secreted bioproducts.

17 Claims, 7 Drawing Sheets

CYTOMETER ON A CHIP

This application claims the benefit of U.S. Provisional Application No. 60/691,951, filed Jun. 17, 2005.

This invention was made with government support under contract NNJ04JA14C awarded by NASA. The government has certain rights to this invention.

FIELD OF THE INVENTION

The disclosed embodiments relate to an assay technique for the determination of phenotype and function of biological cells in a sample using an optical biosensor.

BACKGROUND OF THE INVENTION

Optical techniques that measure cellular phenotype and function most often employ labeled antibodies that specifically label proteins of interest. For example, immunohistochemistry employs samples that have been affixed to a slide and labeled with fluorescently or enzymatically labeled antibodies. Immunohistochemistry has been used in many contexts, including the upregulation of proteins and the characterization of cellular phenotypes. Immunofluorescence microscopy measures antigenic structure with fluorescently labeled antibodies. Uses of this technique include studies of surface expression of proteins in normal and leukemic lymphocytes, and surface protein internalization by activated cells. In confocal microscopy, a laser is scanned across cells labeled with fluorescent antibodies. The specimen is brought into focus by an objective lens and laterally scanned under computer control. Cross-sectional areas are computationally compiled into three-dimensional objects and the subcellular location of labeled proteins is then determined. Confocal microscopy has been used to study antigen expression, apoptosis, and cellular activation.

One of the most common technologies used to phenotype cells is flow cytometry. Flow cytometry measures light scattering, impedance, and fluorescent signals to characterize specific cell types and can identify subpopulations of these cells for sorting. Commercially available flow cytometers measure up to eight different fluorescent molecules bound to a cell, each emitting a distinct wavelength of fluorescent light. Flow cytometers also can measure cellular processes such as cell division, apoptosis, necrosis, and differentiation. Recent developments in flow cytometry sort analyzed cells into microchannels and separate these populations according to fluorescence characteristics.

Flow cytometry has a number of limitations. One drawback is that flow cytometry requires pre-labeling of the cells with fluorescent antibodies or other fluorophores and entails complex experimental protocols that may be difficult to implement in many environments (e.g., resource-poor settings). For flow cytometry to be accurate, the cells must be precisely moved through the center of the focal plane of the illuminating light. This requires a sophisticated system of fluidics, and a narrow orifice in the flow cell (usually in the 50 to 100 micron diameter range). Disturbances in the sample stream can alter the information produced by a flow cytometer, making this technology sensitive to sample clogging and to environmental perturbations. Distinguishing the various cell phenotypes in a sample requires excitation at multiple wavelengths and monitoring of the fluorescence signal in multiple spectral bands. This requires a multi-wavelength laser system and multichannel detection, which results in the need for complex compensation and dramatically increases the number of controls. As multiplexing capacity is increased, adding the required spectral channels substantially increase the complexity, cost, size, power and weight of the instrumentation. More fundamentally, the number of specific phenotypes that can be analyzed in such a system is limited by the number of spectral channels available, which is on the order of 10 in current state-of-the-art flow cytometers.

SUMMARY OF THE INVENTION

As an alternative to flow cytometry and to circumvent some of the drawbacks and limitations listed above, the disclosed embodiments provide a method and system for characterization of cell phenotype and function without the use of fluorescent or other molecular labels (hereafter "label-free"). Another objective is to accomplish the aforementioned objective with a relatively simple, inexpensive, small instrument. Yet another objective is to simultaneously perform measurements on a large number of unique cell interactions for parallel detection of a plurality of phenotypes and cell functional responses in a given sample.

Specific capture ligands for specific cell surface markers of interest are immobilized on a biosensor surface (a biosensor chip) at discrete locations in a predetermined spatial pattern. These discrete locations on the chip will be referred to as cell-capture regions of interest or "cell ROI"s). Binding of cells to the capture ligands in a cell ROI locally changes some measurable properties of the cell ROI and this change is measured with a suitable detection system. The presence of cells in a sample expressing a particular surface phenotype is detected by bringing the sample into contact with the biosensor chip surface and measuring the measureable signals from cell ROIs containing the cognate capture ligand. Including an array of cell ROIs containing specific capture ligands to distinct surface markers provides for the simultaneous detection of a plurality of phenotypes, the identities of which are spatially encoded on the chip. That is, a given phenotype is correlated to a particular address (location) on the chip. A biosensor chip with hundreds or more ROIs provides for highly parallel detection of many cell phenotypes in a given sample.

Specific capture ligands that may be employed include, but are not limited to antibodies, aptamers, specific receptors, MHC-peptide complexes, oligonucleotides, and peptide nucleic acid oligomers. The disclosed embodiments also provide for use of non-specific capture ligands to assess the behavior of mixed cell populations. Examples of non-specific capture ligands include, but are not limited to antibodies against species-specific antigens and anti-MHC antibodies.

Measuring the binding of cells to a cell ROI is accomplished by measuring the localized measurable response of each cell ROI, preferably with a system that permits parallel measurement from all ROIs. Examples of biosensor surfaces include a metal-coated optical grating, which upon illumination by light of the appropriate wavelength and polarization couples incident light into surface plasmons on the metal at an appropriate angle of incidence (resonant condition), which is related to the number of cells bound to the ROI. Other applicable biosensing approaches are well known in the art and include planar waveguide devices, resonant mirrors, guided-mode resonant filters and resonant acoustic devices.

In addition to spatially sorting cells based on cell phenotype, another objective is to measure cellular responses in real time or near real time without the use of molecular labels. Cells respond to environmental stimuli in a variety of ways (e.g., altering shape, secreting bioproducts, such as cytokines, lysing, undergoing programmed cell death, etc). The disclosed embodiments provide for detection of cellular responses to stimuli by including on the biosensor surface sets of secondary ROIs containing capture ligands to specific cell bioproducts. These "response ROIs" (to be distinguished from cell ROIs) are strategically placed in close proximity to and in predetermined spatial patterns relative to cell ROIs and may overlap the cell ROIs. The shape, location and pattern of cell ROIs and response ROIs are designed to generate spatial and temporal optical signatures which provide information on cell phenotype and function (e.g., secretion of cytokines), in near real time in a highly multiplexed label-free manner. Since a biosensor chip can accommodate hundreds or more ROIs, the disclosed embodiments provide for highly parallel detection of many cell phenotypes and associated functional responses in a given sample.

Types of cells that can be analyzed with the disclosed embodiments include, but are not limited to, mammalian cells, plant cells and bacteria. Applications are broad and encompass many fields such as biodefense, clinical diagnostics, environmental toxicology and drug discovery research. Some examples of specific applications include bioassays to detect the presence of toxic or activating compounds, assessment of responses to pharmaceutical drugs, assessment of host/pathogen interactions and assessment of immune function. Assays may be conducted in small volumes, on the order of 10 microliters, enabling minimally invasive diagnostic tests from samples obtained, for example, by finger stick using a medical lancet as is routinely done by diabetics when monitoring blood glucose.

DESCRIPTION OF THE DISCLOSED EMBODIMENTS

The following examples are given to illustrate various embodiments and aspects of the invention and are not intended to limit the claims in any manner whatsoever.

Figure 1:
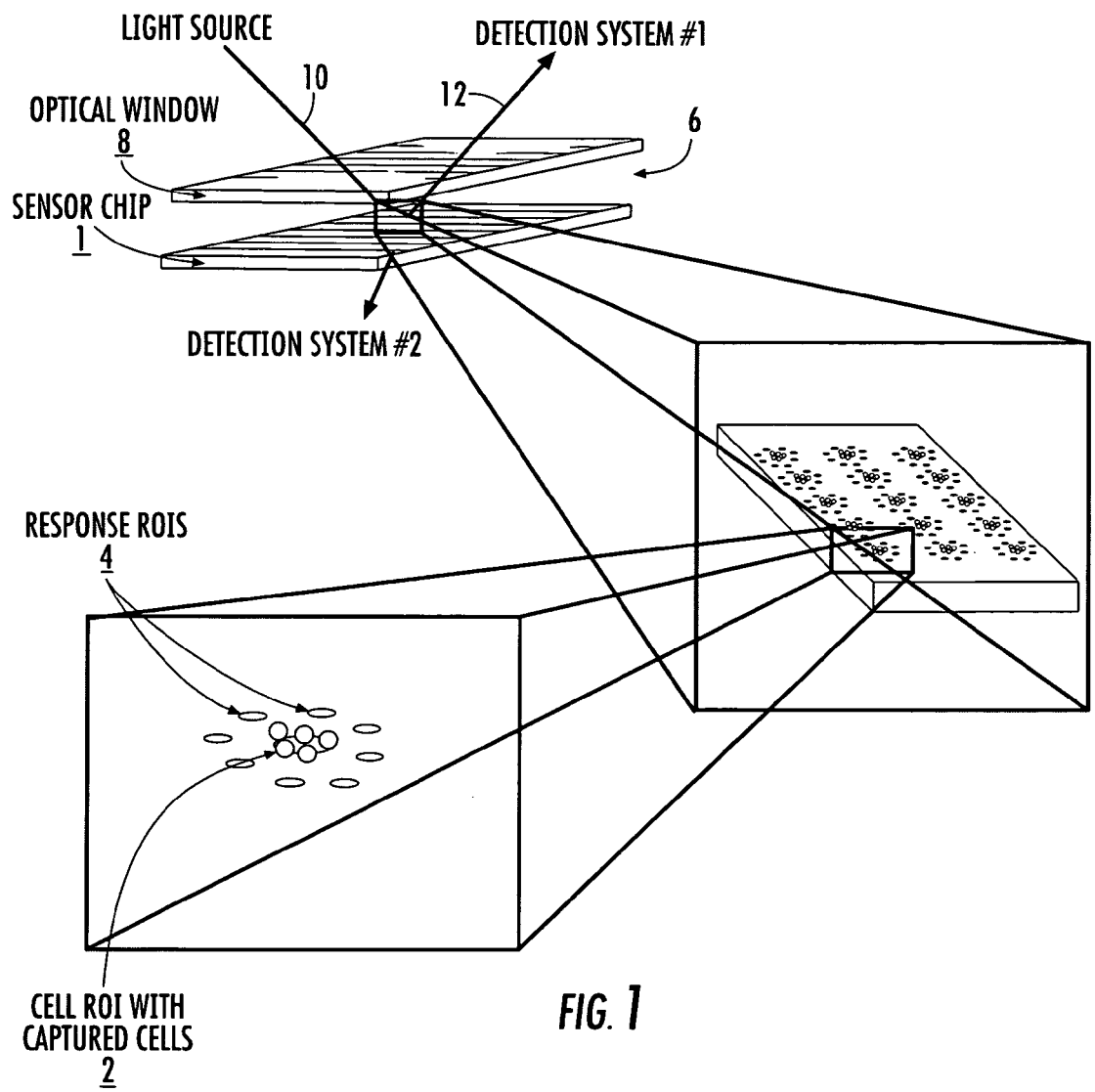
FIG. 1 illustrates in diagrammatic form an embodiment of an apparatus for measuring cell phenotype and cellular responses with a surface plasmon resonance optical measurement system.

FIG. 1 illustrates an apparatus for measuring cell phenotype and cellular responses including a biosensor chip 1 onto which the cell ROIs 2 and the Response ROIs 4 are deposited in predetermined spatial patterns. A flow cell 6 that contains the biosensor chip 1, brings a sample into contact with the biosensor surface, provides a chamber for incubating cells during the course of an experiment, and provides a window 8 for optical interrogation. An optical detection system provides an illumination beam 10 and detects the reflected light 12 from the chip to measure the binding of cells and bioproducts to their cognate ROIs. One method of optical interrogation of analyte (cell or bioproduct) binding to the chip is based on the phenomenon of surface plasmon resonance (SPR). An SPR chip typically includes a reflection-type metallic grating to couple an incident light beam with surface plasmons in the metal. This coupling approach makes it possible to directly illuminate the sensor surface through the sample, which allows imaging of the entire chip and thus simultaneous measurement of hundreds of interactions at the chip surface. In a preferred embodiment the transducer chip is a gold-coated plastic (polycarbonate) grating with a grating period of approximately 600 to 900 microns and a groove depth of approximately 50 to 80 nm. Illumination is provided by a single light-emitting diode (LED) with peak emission in the range of 650 to 900 nm and detection is provided by an imaging device such as a CCD or CMOS camera.

The principle of operation is as follows. For collimated, monochromatic, p-polarized light incident on the chip at angle θ, through a dielectric medium of refractive index n, the x-component (the x-axis is along the gold surface and in the direction perpendicular to the grating grooves) of the lightwave vector, $k_{mx}$ associated with m-th order diffracted light is given by:

$$k_{mx} = \frac{\omega}{c} n \sin\theta + m k_g \qquad (1)$$

where ω is the angular optical frequency, c the speed of light in vacuum, and $k_g$ denotes the grating wave vector, which is along the x-direction ($k_g=2\pi/\Lambda$, where Λ is the grating period). The wave vector of the surface plasmons is given by:

$$k_{sp} = \frac{\omega}{c} \sqrt{\frac{\varepsilon_m n}{\varepsilon_m + n^2}} \qquad (2)$$

where $\varepsilon_m$ is the dielectric constant of the gold and n is the index of refraction of the adjacent dielectric layer (sample). At the incident angle, $\theta_R$, for which resonance occurs, $k_{mx}$, the x-component of the wave vector associated with the diffracted wave of the exciting light must be equal to the wave vector of the surface plasmon. That is:

$$\frac{\omega}{c} n \sin\theta_R + mk_g = \frac{\omega}{c} \sqrt{\frac{\varepsilon_m n^2}{\varepsilon_m + n^2}} \quad (3)$$

As Eq. (3) shows, for a given grating design and diffraction order, the SPR angle, $\theta_R$, is very sensitive to variation of the refractive index of the dielectric adjacent to the gold layer supporting the surface plasmon wave. The energy of the excited surface plasmons is taken from incident light causing the intensity of the zeroth order diffracted beam to decrease. The grating period $\Lambda$ is designed such that for the optical wavelength used, resonance can be achieved at a relatively small angle of incidence (near normal to the chip) to facilitate imaging of the entire chip.

This embodiment provides for measurement of multiple specific binding events in parallel. For example, antibodies with the desired specificity are spotted on the gold-coated sensor chip in a microarray format to form ROIs. Interrogating light is directed onto the chip surface at a series of incident angles and the zeroth order diffracted light (specular reflection) intensity is quantitatively imaged onto a CCD camera at each angle of incidence. The reflected intensity from each ROI is a function of the incoming light's incident angle, the local index of refraction at the surface, and the amount of analyte bound. The SPR angle (incident illumination angle at which the reflected light is at a minimum) changes locally at each ROI as the mass of analyte bound to the ROI changes.

The acquired images are processed in software to determine the SPR angles for all ROIs on the chip and the process is repeated through the duration of a measurement cycle to provide a time course of analyte binding (binding kinetics) to each ROI. Specific binding events between cellular surface antigens and immobilized ligands or between secreted bioproducts and their cognate ligands are detected by a shift in the SPR angle at the respective ROIs.

Figure 2:
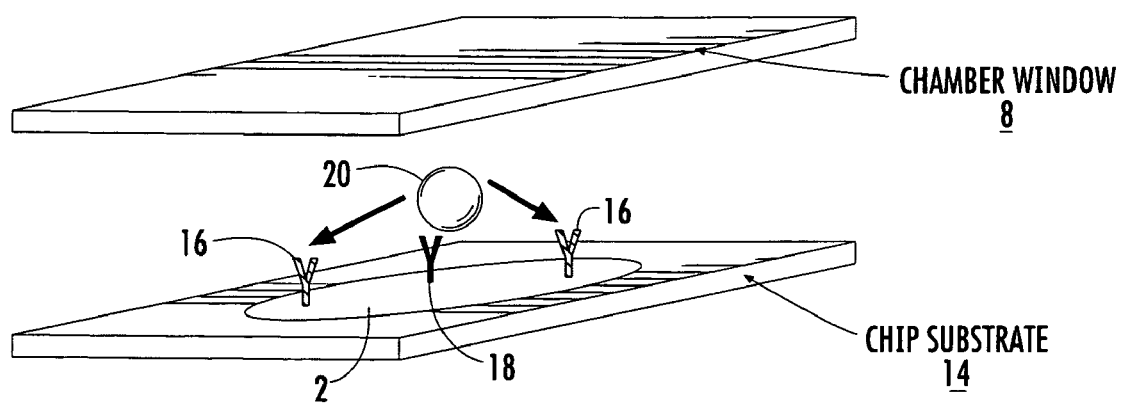
FIG. 2 shows in schematic form a configuration for the deposition of capture ligand regions on a biosensor chip.

An illustration of a basic ROI design according to a first embodiment is shown in FIG. 2. This figure illustrates a single ROI which functions as both a cell ROI and a Response ROI since capture ligands for both cells and bioproducts are co-mingled on a single overlapping spot on the chip. FIG. 2 schematically shows the gold-coated plastic grating chip substrate 14, the optical window 8 above the chip which provides optical access for measurements and defines the upper flow cell boundary, and a circular ROI 2 which contains immobilized bioproduct capture antibody 16 and cell capture antibody 18. For illustration purposes, FIGS. 2 to 6 show only one cell capture antibody 18, one captured cell 20 and two anti-bioproduct antibodies 16 at the ROI 2. In practice the ROIs would contain a large number of each type of antibody and one or more cells would be typically captured. In the configuration of FIG. 2, cells are captured by immobilized antibody against surface determinants and cultured on the chip surface. As the captured, cultured cells 20 secrete or release proteins or other macromolecules, those molecules are captured by the corresponding cognate antibodies 16 intermixed with the cell capture antibodies 18 in the same ROI 2. Initial changes in optical or sensing properties at the ROI when sample is first flowed over the chip reflect the capture of cells of the appropriate surface phenotype. Unbound cells are then washed from the flow compartment (chamber). Subsequent intensity changes at the ROI during incubation of the captured cells reflect levels of secreted or released molecules or changes in cellular phenotype. Another measure of secretion levels could be assessed by measurement of the distances from the source cell at which SPR shifts can be measured.

Figure 3:
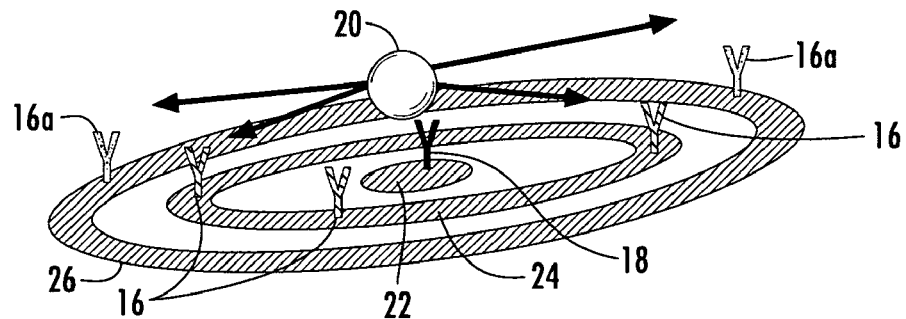
FIG. 3 shows in schematic form a second configuration for the deposition of capture ligand regions on a biosensor chip.

An alternative configuration is illustrated in FIG. 3. In this configuration, cells 20 are captured on a central cell ROI 22 by immobilized antibody 18 against cell surface determinants and cultured on the chip surface. As the captured cells 20 secrete or release proteins or other macromolecules, some of those molecules are captured by a first set of bioproduct capture antibodies 16 deposited on a first surrounding circular response ROI 24 concentric with the central cell ROI 22. Another set of released or secreted macromolecules is captured by a second set of bioproduct capture antibodies 16a immobilized on a second concentric circular response ROI 26 of larger diameter. In this configuration, distinct, multiple secreted protein responses may be simultaneously characterized.

Figure 4:
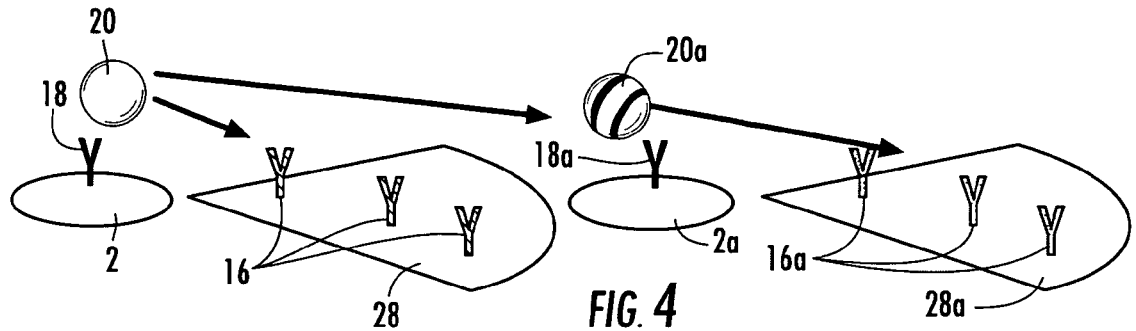
FIG. 4 shows in schematic form a third configuration for the deposition of capture ligand regions on a biosensor chip.

A further alternative configuration is shown in FIG. 4. In this configuration, multiple sets of interacting ROIs are created. In each set, two cell ROIs 2 and 2a, with their corresponding response ROIs 16 and 16a are placed in proximity to enable the study of cell-cell interactions. A primary responding cell population 20 is captured by immobilized antibody 18 against cell surface determinants on a primary cell ROI 2 and cultured on the chip surface. A secondary cell ROI 2a captures a second type of cell 20a with antibodies to secondary-cell-specific surface determinants 18a. As the primary cells 20 secrete or release a first set of proteins or other macromolecules, some of these molecules are captured by antibodies 16 immobilized on an adjacent downstream response ROI 28. Secondary cells 20a captured in ROI 2a that are responsive to some of the soluble molecules secreted by the primary cells 20 may produce a secondary response by secreting or releasing a second set of protein or other macromolecules, some of which may be captured by a second downstream response ROI 28a. Measurements of the intensities, spatial distribution, and temporal responses of SPR signals from the primary 28 and secondary 28a bioproduct ROIs provide functional information on both primary and secondary cells 20, 20a and their interaction. Although FIG. 4 illustrates only one set of interacting ROIs it should be clear that a biosensor chip will generally contain a large array of such sets, permitting the parallel characterization of multiple functional responses and cell-cell interactions.

Figure 5:
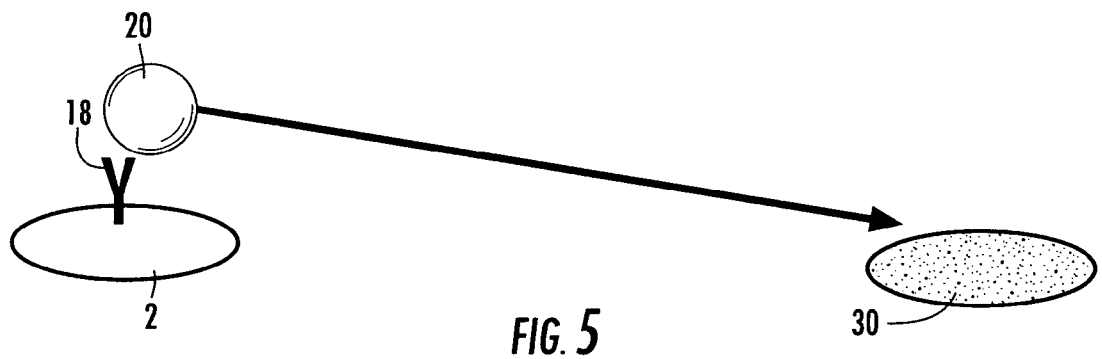
FIG. 5 shows in schematic form a fourth configuration for the deposition of capture ligand regions on a biosensor chip.

A further alternative ROI configuration is illustrated in FIG. 5. In this configuration a primary cell population 20 is captured on a cell ROI 2 by immobilized antibody 18 against cell surface determinants and cultured on the chip surface. As the captured cells 20 secrete or release enzymes, those proteins are detected by the effect they have on a substrate 30 that is localized downstream of the captured cells. An example of a substrate would be a biomolecules with a moiety that is cleaved by the released enzyme leading to a change in SPR signal.

Figure 6:
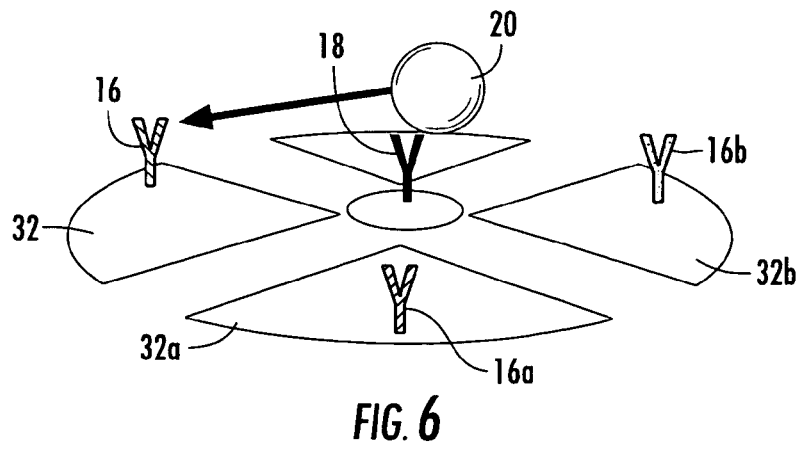
FIG. 6 shows in schematic form a fifth configuration for the deposition of capture ligand regions on a biosensor chip.

FIG. 6 illustrates a still further alternative ROI configuration. In this configuration, the responding cell population 20 is captured by immobilized antibody 18 against cell surface determinants and cultured on the chip surface. As the captured cells 20 secrete or release proteins or other macromolecules, those molecules are detected by the surrounding response ROIs 32, 32a, 32b. Each of the surrounding response ROIs is populated with antibodies 16, 16a, 16b against a different target, so intensity and spatial signal distribution provides information on identity and concentration of the respective secreted products. Changes of the ROI properties with respect to time may provide additional information on the dynamics of the cellular responses. In a grating coupled surface plasmon resonance chip, the intensity of the reflected light will vary according to changes in the optical properties of the chip surface at the ROIs due to capture of cells or cell products.

Figure 7:
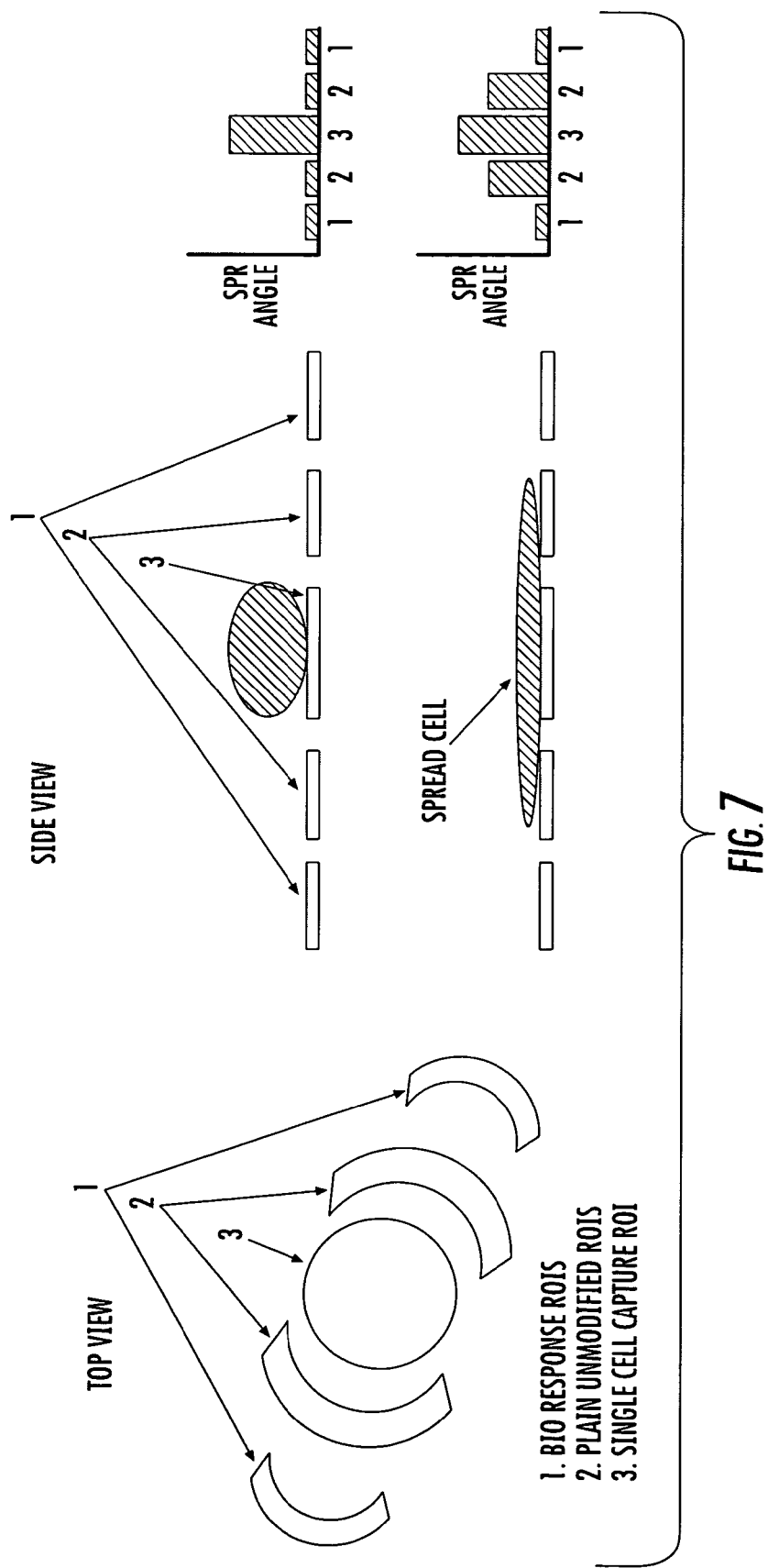
FIG. 7 includes top and side views of a second apparatus for measuring cell phenotype and measuring cellular responses including changes in cell shape.

FIG. 7 (top view) illustrates one possible configuration for detection of cell shape changes in addition to detection of secreted or released bioproducts. In this configuration a cell capture ROI (3) of sufficiently small dimensions to capture only a single cell is surrounded by a proximal set of shape sensing ROIs (2) that do not contain capture ligands, and by a second distal set of response ROIs (1) containing immobilized capture ligand to target analytes that may be secreted or released by the cell captured in the cell ROI (3). FIG. 7 (side view) illustrates the mechanism for detection of a cell shape change: when a rounded cell is captured on the cell ROI (3) (upper left panel), the optical signal from this ROI changes accordingly (illustrated in the upper right panel as an increase in SPR angle according to one possible sensor embodiment) but the signals from the adjacent shape sensing ROIs (2) remain at baseline level. A change in cell phenotype to a flattened shape (lower panel) whereby portions of the cell overlap the shape sensing ROIs (2) leads to an increase in optical signal at these ROIs, as illustrated in the lower right panel.

Figure 8:
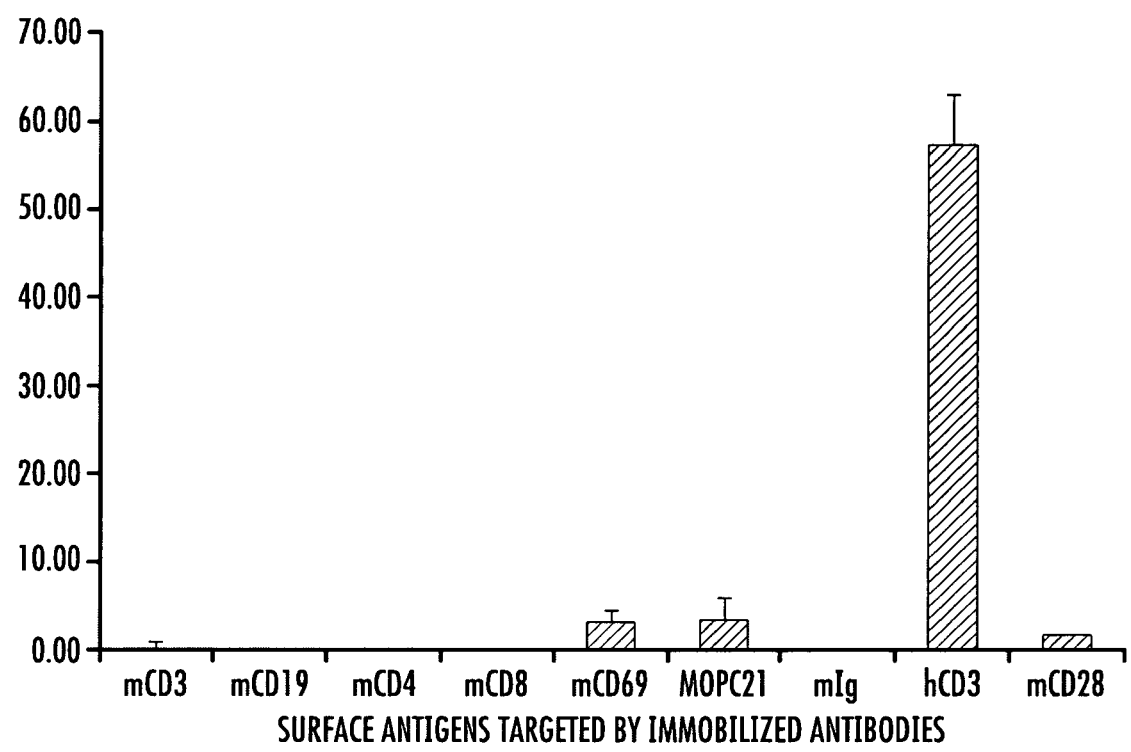
FIG. 8 is a bar graph showing capture and label-free detection of phenotypic-specific cells in a sample according to the present invention.
Figure 9:
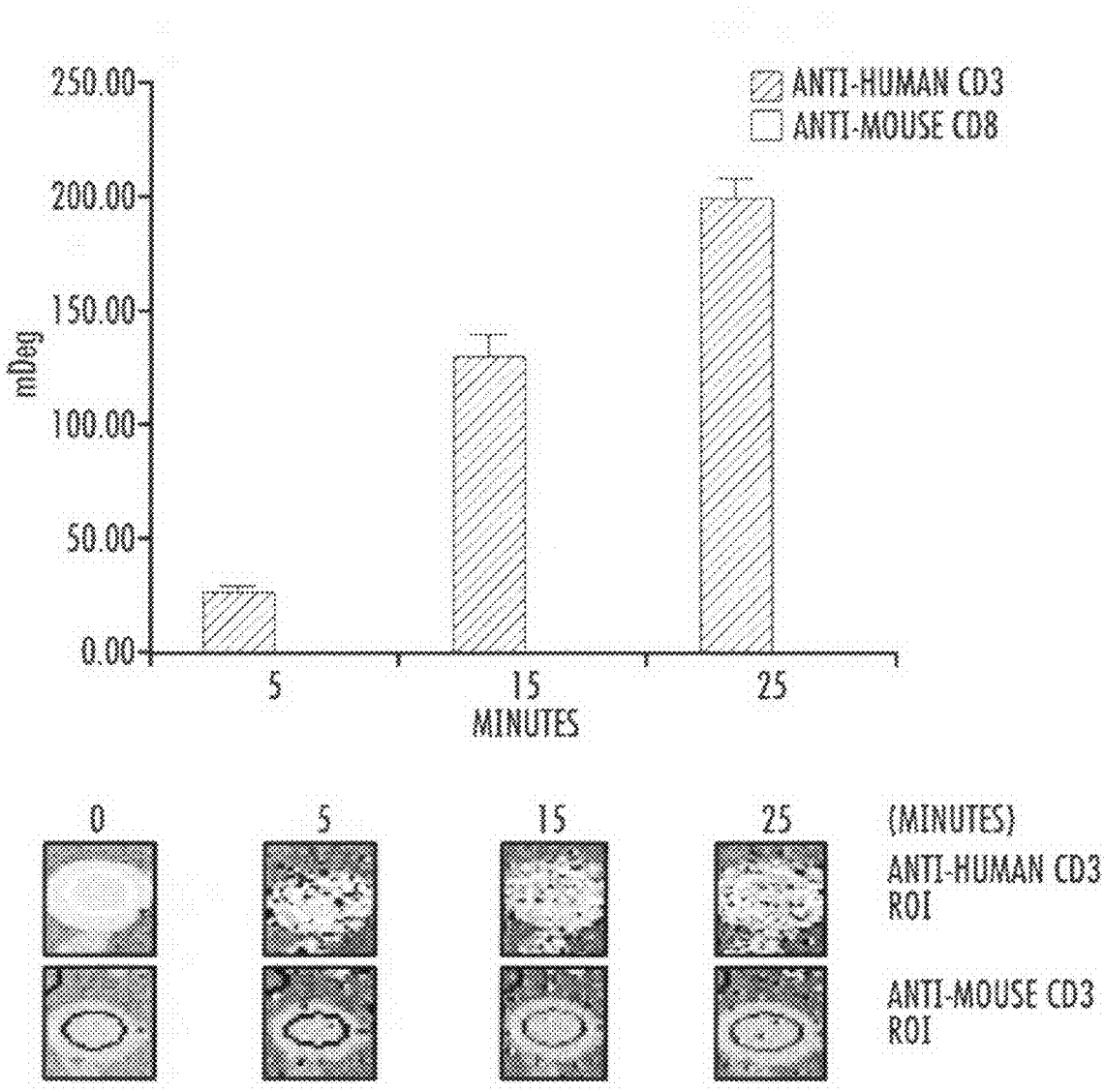
FIG. 9 shows a bar graph demonstrating real time, label-free detection of phenotypic-specific cells according to this invention and a set of images showing the number of captured cells on the biosensor chip.

FIG. 8 illustrates detection of the capture of cells in a sample based on the expression of specific cell surface markers. The human cell line Jurkat T cells, which express the surface marker CD3∈ were passed across ROIs containing immobilized anti-human CD3∈ monoclonal antibodies and negative control antibodies that bind proteins not present on Jurkat T cells. As evidenced by the observed SPR angle shifts, Jurkat T cells were only captured by the anti-human CD3∈ monoclonal antibody ROIs. FIG. 9 shows that the signals from these ROIs exhibit a time-dependent increase over the duration of Jurkat T cell flow across the chip reflecting increasing capture of cells with time. Images of the chip also show a time-dependent increase in the capture of cells at the specific cell capture ROIs but do not show cell capture at irrelevant ROIs (FIG. 9).

Figure 10:
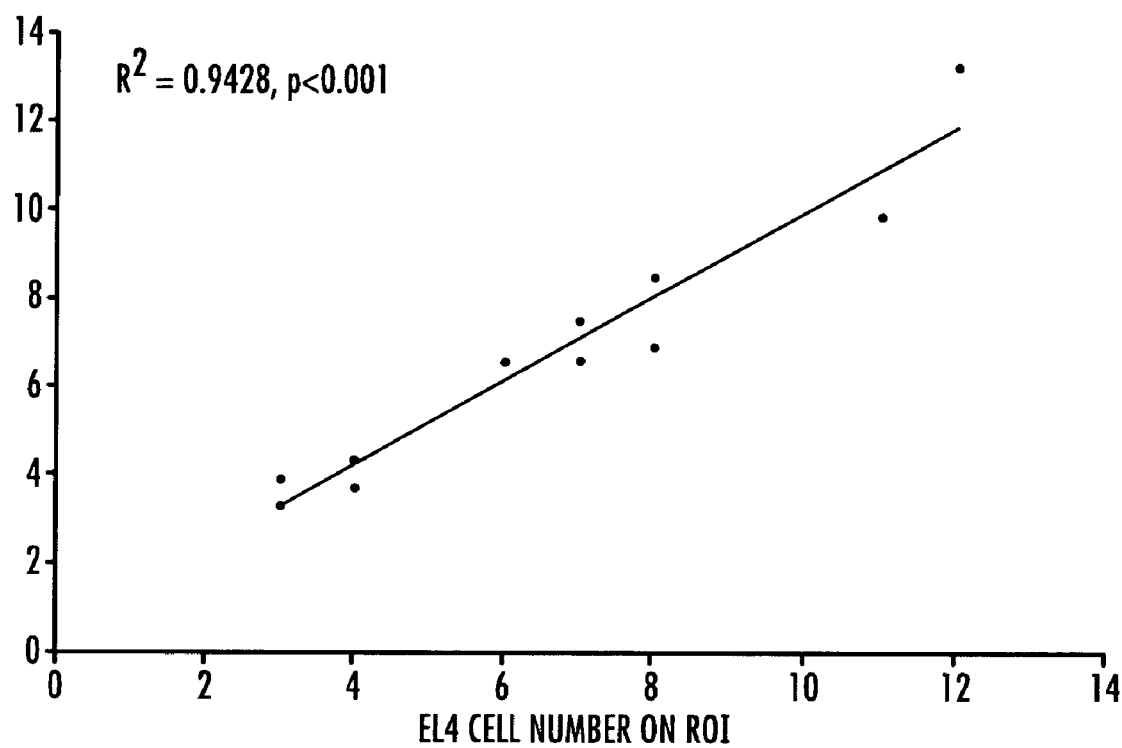
FIG. 10 is a graph plotting measured SPR angle shift value against the number of observed cells on a region of interest (ROI) on the biosensor chip to illustrate quantitative measurement of cell capture according to the invention.

Measurements shown in FIG. 10 demonstrate that there is a linear relationship between the number of captured cells at an ROI and the measured SPR angle shift. EL4 is a mouse T cell lymphoma that can be captured by immobilized anti-mouse CD3∈ monoclonal antibody. FIG. 10 shows an experiment in which mouse T cell lymphoma cells EL4 were flowed across a chip containing anti-mouse CD3∈ antibody capture ROIs. Each cell captured caused an SPR angle shift of approximately 1 millidegree. The data presented in FIG. 10 show that there is a direct correlation between SPR angle shift and the number of cells captured.

Figure 11:
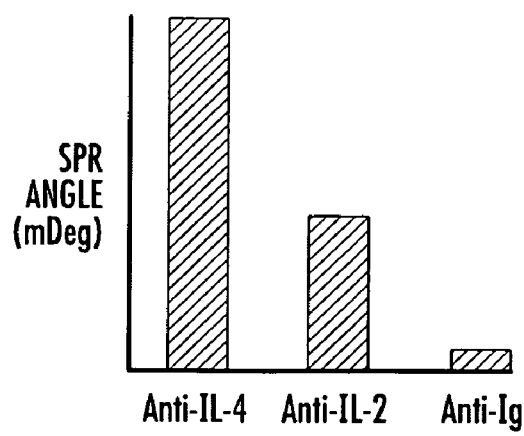
FIG. 11 is a bar graph showing SPR angle shift at three different regions of interest (ROIs) on a biosensor chip to illustrate quantitative, real time, label-free measurement of cytokine secretion by cultured cells.

The data presented in FIG. 11 show the capability for label-free measurement of cell responses in near real time. In this experiment, activated Jurkat T cells were incubated on the chip surface, and response (ROIs) comprised of anti-cytokine (IL-2 and IL-4) and anti-immunoglobulin antibodies were interrogated over time. The production of IL-2 and IL-4 cytokine was detectable above background after only 20 minutes of assessment. As expected, the signal from the anti-IgG ROIs did not change significantly from background levels.

What is claimed is:

1. A method for detecting in an aqueous sample a plurality of cell populations each expressing at least one distinct cell surface marker and for assessing the functional status of said cell populations, said method comprising the steps of:
   i. providing a sensor surface having optical properties that change in response to binding of material to the surface or to molecular adlayers on the surface;
   ii. creating one or more cell capture regions on said sensor surface by immobilizing cell capture ligands specific to said cell surface markers in a predetermined spatial pattern;
   iii. creating one or more cell product capture regions on said sensor surface by immobilizing cell product capture ligands, each said cell product capture ligand being specific to a secreted or released product from said cell populations, said one or more cell product capture regions arranged in predetermined spatial patterns proximal to or overlapping one or more of said cell capture regions;
   iv. contacting said sensor surface with the aqueous sample containing living cells, cells expressing a cell surface marker specific to said cell capture ligands being captured at said cell capture regions, captured cells forming a pattern corresponding to the predetermined spatial pattern of said one or more cell capture regions;
   v. detecting changes in said optical properties at each of said cell capture regions, the magnitude of the detected change at each cell capture region being a function of the number of cells captured at said each cell capture region;
   vi. replacing the aqueous sample with a biological buffer comprising a culture medium and incubating the captured cells on said sensor surface, cell products secreted or released from said captured cells being captured at cell product capture regions having a cell product capture ligand specific to said cell products, captured cell products forming a pattern corresponding to the predetermined spatial patterns of said one or more cell product capture regions;
   vii. monitoring changes in said optical properties at each of said cell product capture regions over time, the magnitude of the change in optical properties at each said cell product capture region being a function of the quantity of the secreted or released product from said captured cells captured at each of said cell product capture regions; and
   viii. using the detected changes of the optical properties of the sensor surface at said cell capture regions and said cell product capture regions to provide information on cell functions of said captured cells over time.

2. The method of claim 1, wherein said step of providing a sensor surface comprises:
   providing a grating coupled surface plasmon resonance chip having a sensor surface wherein said optical properties are a refractive index.

3. The method of claim 2, wherein said step of detecting changes in said refractive index comprises:
   illuminating the sensor surface with light of a substantially constant wavelength at a plurality of incident angles; and
   measuring an intensity of the zeroth order diffracted light at each angle of incidence from each of said cell capture regions and cell product capture regions.

4. The method of claim 1, wherein the sensor surface is based on evanescent waveguide sensing.

5. The method of claim 1, wherein the step of contacting the sensor surface with the aqueous sample is performed for a predetermined period of time.

6. The method of claim 1, wherein the step of creating one or more cell capture regions on said sensor surface comprises:
   creating a plurality of cell capture regions, said plurality of cell capture regions including first cell capture regions having first cell capture ligands specific to cell surface markers for capturing a first cell population and second cell capture regions having second cell capture ligands specific to cell surface markers for capturing a second cell population distinct from said first cell population.

7. The method of claim 6, wherein said step of creating a plurality of cell capture regions comprises:

arranging said first and second cell capture regions in predetermined spatial patterns, whereby each of said first and second cell populations are correlated to a known location on said sensor surface.

8. The method of claim 6, comprising the steps of:

selecting said first and second cell populations wherein said second cell population responds to a first secreted or released cell product from said first cell population by secreting or releasing a second cell product;

wherein said step of creating one or more cell product capture region comprises:

creating at least one cell product capture region in proximity to or overlapping one or more of said second cell capture regions, said at least one cell product capture region including a cell product capture ligand specific to said second cell product; and said step of using the detected changes of the optical properties at said cell capture regions and said cell product capture regions provides information on the function of said first and second cell populations and their interaction.

9. The method of claim 6, comprising the steps of:

positioning said sensor surface in a flow cell which defines a flow path for said aqueous sample and said biological buffer and a chamber for incubating the captured cells, said flow cell also including a window permitting optical interrogation of said sensor surface;

said step of creating one or more cell product capture regions comprises:

locating at least one of said one or more cell product capture regions so that said aqueous sample or said biological buffer contacts at least one of said one or more cell capture regions before contacting said at least one cell product capture region.

10. The method of claim 1, wherein the step of contacting the sensor surface with the aqueous sample is performed for a predetermined period of time and the detected change in optical properties at each of said cell capture regions is used to calculate the concentration of cells having the cell surface marker at each said cell capture region in said aqueous sample.

11. The method of claim 1, wherein the step of creating one or more second capture regions comprises:

creating a plurality of cell product capture regions proximal to at least one cell capture region, at least one of said plurality of said cell product capture regions including a cell product capture ligand different from a cell product capture ligand of another of said plurality of cell product capture regions.

12. The method of claim 11, wherein said method comprises;

detecting changes in said optical properties at each of said plurality of cell product capture regions over time, whereby the presence and concentration of different secreted or released cell products are measured with respect to time.

13. The method of claim 1, wherein said step of creating one or more cell capture regions comprises:

creating at least one cell capture region configured to capture a single cell.

14. The method of claim 1, wherein said method comprises:

detecting changes in said optical properties of said sensor surface in proximity to at least one of said cell capture regions over time, whereby changes in the shape of one or more cells captured on said at least one cell capture region are measured with respect to time.

15. The method of claim 1, wherein said step of creating one or more cell product capture regions comprises:

creating at least one cell product capture region overlapping with at least one of said cell capture regions, said cell capture ligands of said at least one cell capture region and said cell product capture ligands being intermingled in a single overlapping region on said sensor surface.

16. The method of claim 15, wherein said step of detecting changes in said optical properties of said cell capture regions comprises:

detecting changes in the optical properties of said single overlapping region before said step of replacing the aqueous sample with a biological buffer and incubating the captured cells, said changes being a function of the number of cells captured at said single overlapping region; and detecting changes in the optical properties of said single overlapping region during incubation of said captured cells, said changes in the optical properties of said single overlapping region during incubation being a function of at least one of the quantity of secreted or released cell products captured at said single overlapping region and changes in cell shape.

17. The method of claim 1, comprising the step of:

exposing the cells captured at one or more of said cell capture regions to a stimuli;

detecting changes in the optical properties of said cell capture regions and said cell product capture regions; and using the detected changes in said optical properties at said cell capture regions and said cell product capture regions to provide information on the response of said captured cells to said stimuli.

* * * * *